United States Patent [19]

Asselin et al.

[11] Patent Number: 4,562,200

[45] Date of Patent: Dec. 31, 1985

[54] 5(INDOLYL) AND 5(2,3-DIHYDROINDOLYL) SUBSTITUTED AMINOETHANOLS AND THEIR USE AS ANTI-HYPERTENSIVES

[75] Inventors: Andre A. Asselin, St. Laurent; Danilo A. Crosilla, Ile Bizard; Leslie G. Humber, Dollard-des-Ormeaux, all of Canada

[73] Assignee: American Home Products Corporation, New York, N.Y.

[21] Appl. No.: 648,418

[22] Filed: Oct. 23, 1984

Related U.S. Application Data

[62] Division of Ser. No. 509,888, Jun. 30, 1983, Pat. No. 4,521,606.

[51] Int. Cl.[4] .................... A16K 31/40; C07D 209/12
[52] U.S. Cl. .................................. 514/415; 548/491; 548/503; 546/165
[58] Field of Search ................. 548/491, 503; 514/415

[56] References Cited

U.S. PATENT DOCUMENTS

| 4,012,444 | 3/1977 | Lunts et al. | 424/324 X |
| 4,252,803 | 2/1981 | Webb | 424/248.5 |
| 4,346,093 | 8/1982 | Friebe et al. | 548/503 |
| 4,348,398 | 9/1982 | Atkinson et al. | 424/258 |

FOREIGN PATENT DOCUMENTS

2370472 7/1978 France .
1565080 4/1980 United Kingdom .

*Primary Examiner*—Glennon H. Hollrah
*Assistant Examiner*—D. B. Springer

[57] ABSTRACT

Herein is disclosed bicyclic-substituted aminoethanol derivatives, therapeutically acceptable acid addition salts thereof, processes for their preparation, methods of using the derivatives and pharmaceutical compositions. The derivatives are useful for treating hypertension in a mammal.

6 Claims, No Drawings

5(INDOLYL) AND 5(2,3-DIHYDROINDOLYL) SUBSTITUTED AMINOETHANOLS AND THEIR USE AS ANTI-HYPERTENSIVES

This is a division of application Ser. No. 509,888, filed June 30, 1983, now U.S. Pat. No. 4,521,606, issued June 4, 1985.

BACKGROUND OF THE INVENTION

This invention relates to novel bicyclic-substituted aminoethanol derivatives, to therapeutically acceptable acid addition salts thereof, to processes for their preparation, to methods of using the derivatives and to pharmaceutical compositions of the derivatives. These derivatives are useful for treating hypertension in a mammal.

A number of antihypertensive cyclic-aminoethanol derivatives are known and described, for example, C. F. Webb, U.S. Pat. No. 4,252,803, Feb. 24, 1981; Great Britain Patent Specification No. 1,565,080, Apr. 16, 1980; Derwent Publications Ltd., Farmdoc 57223A for French Pat. No. 2,370,472, July 13, 1978; L. H. C. Lunts et al., U.S. Pat. No. 4,012,444, Mar. 15, 1977; and J. Atkinson et al., U.S. Pat. No. 4,348,398, Sept. 7, 1982.

The reported known compounds differ from the chemical structure of the compounds of the present invention by having different substitutions on the cyclic-aminoethanol system.

SUMMARY OF THE INVENTION

The compounds of this invention are represented by formula I

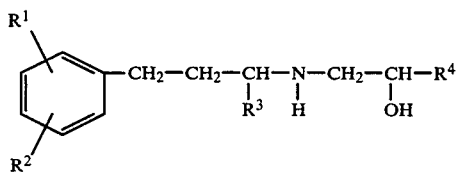

in which $R^1$ and $R^2$ each is hydrogen, halogen or lower alkoxy, or adjacent $R^1$ and $R^2$ are joined together to form a methylenedioxy chain; $R^3$ is lower alkyl containing one to three carbon atoms; and $R^4$ is a heterocycle selected from the group consisting of

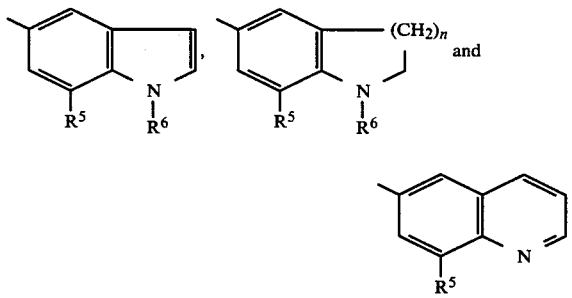

wherein n is the integer 1 or 2; $R^5$ is cyano, aminocarbonyl, methylthio, methylsulfinyl, methylsulfonyl or aminosulfonyl; and $R^6$ is hydrogen or lower alkyl; or a therapeutically acceptable acid addition salt thereof.

A preferred group of compounds of this invention is represented by formula I in which $R^1$ and $R^2$ each is hydrogen or lower alkoxy, or adjacent $R^1$ and $R^2$ are joined together to form a methylenedioxy chain; $R^3$ is methyl; and $R^4$ is the heterocycle

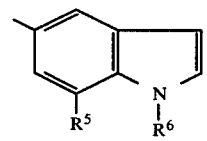

wherein $R^5$ is aminocarbonyl; and $R^6$ is hydrogen or lower alkyl.

A pharmaceutical composition is provided by combining a compound of formula I, or a therapeutically acceptable acid addition salt thereof, and a pharmaceutically acceptable carrier.

The compounds of this invention can be used to treat hypertension in a hypertensive mammal by administering to the mammal an effective antihypertensive amount of a compound of formula I or a therapeutically acceptable acid addition salt thereof.

DETAILED DESCRIPTION OF THE INVENTION

The term "lower alkyl" as used herein means straight and branched chain alkyl radicals containing from one to six carbon atoms, preferably one to four carbon atoms, and includes methyl, ethyl, propyl, 1-methylethyl, butyl, 1,1-dimethylethyl, pentyl and the like, unless stated otherwise.

The term "halogen" as used herein means halo radicals and includes fluoro, chloro, bromo and iodo, unless stated otherwise.

The term "lower alkoxy" as used herein means straight chain alkoxy radicals containing from one to six carbon atoms and branched chain alkoxy radicals containing three to six carbon atoms and includes methoxy, ethoxy, 1-methylethoxy, butoxy, hexoxy and the like.

The term "complex borohydride" as used herein means the metal borohydrides and includes, for example, sodium borohydride, sodium cyanoborohydride, potassium borohydride, lithium borohydride, zinc borohydride, lithium triethylborohydride and the like.

The term "lower alkanol" as used herein means both straight and branched chain alkanols containing from one to four carbon atoms and includes methanol, ethanol, 1-methylethanol, butanol and the like.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanoldiethyl ether mixture.

These salts, when administered to a mammal, possess the same pharmacologic activities as the corresponding bases. For many purposes it is preferable to administer the salts rather than the basic compounds. Suitable acids to form these salts include the common mineral acids, e.g. hydrohalic, sulfuric or phosphoric acid; the organic acids, e.g. maleic, citric or tartaric acid; and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included within the scope of this invention are all isomeric forms of Formula I. Such isomers include the mixtures of enantiomers or diastereomers as well as individual enantiomers or diastereomers of formula I.

The antihypertensive effect of the compounds of formula I or a therapeutically acceptable acid addition salt thereof is demonstrated in standard pharmacological tests, for example, in tests conducted in the spontaneously hypertensive rat (SHR). The latter test method is as follows: Male rats, Okamoto-Aoki Strain, ranging in weight between 250–400 g were anesthetized with diethyl ether. Their left femoral arteries and veins were cannulated with polyethylene tubing of the appropriate size. Each animal was then enfolded in a rubber mesh jacket which was secured with 4 towel clamps. The animal was suspended via the towel clamps from a bar and allowed to recover from the anesthesia. The femorial arterial cannula was connected to a Stratham pressure transducer (Model P23, Gould Stratham Instruments, Hato Rey, Porto Rico), which in turn was attached to a polygraph for recording the mean arterial blood pressure and pulse rate. The pulse rate was considered to be the heart rate. The test compound was administered by gastric gavage in a volume of 5 ml/kg. Heart rate and blood pressure were noted at 5, 10, 15, 30, 45 and 60 minutes and hourly thereafter for a period of at least 4 hours after drug administration.

Using this method, the following representative compound of formula I was effective for reducing the blood pressure (BP) in the spontaneously hypertensive rat: 5-[1-hydroxy-2-[(1-methyl-3-phenylpropyl)amino]-ethyl]-1H-indole-7-carboxamide at a dose of 5 mg/kg of body weight caused a 31% decrease in BP at 0.75 hour.

The compounds of formula I of this invention are used alone or in combination with pharmacologically acceptable carriers, the proportion of which is determined by the solubility and chemical nature of the compound, chosen route of administration and standard biological practice. For example, they are administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I can contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as antihypertensive agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective antihypertensive amount of the compounds for oral administration can usually range from about 0.5 to 100 mg per kilogram body weight per day in single or divided doses although as aforementioned variations will occur. However, a dosage level that is in the range of from about 1.0 to 50 mg per kilogram body weight per day in single or divided doses is employed most desirably for oral administration in order to achieve effective results.

The compounds of formula I also can be used to produce beneficial effects in the treatment of hypertension, peripheral and cerebral vascular diseases and related disorders when combined with a second therapeutic agent comprising a therapeutically effective amount of a diuretic and/or antihypertensive agent commonly used in antihypertensive therapy. Such diuretic and/or antihypertensive therapeutic agents include, for example, the thiazide diuretics for instance, chlorothiazide or hydrochlorothiazide; mineralocorticoid antagonizing diuretic agents, e.g., spironolactone; and other diuretics such as triameterene and furosemide. Examples of still other suitable antihypertensive agents are prazosine, hydralazine and centrally active antihypertensive agents such as methyldopa, clonidine, and reserpine; as well as the $\beta$-adrenergic blocking agents, for instance, propranolol. The compound of formula I can be administered sequentially or simultaneously with the antihypertensive and/or diuretic agent. Preferred antihypertensive and/or diuretic therapeutic agents are the antihypertensive agents such as the thiazides, mineralocorticoid antagonizing diuretic agents and the $\beta$-adrenergic blocking agents. A combination of the foregoing antihypertensive agents are well known in the art; for instance, "Physician Desk Reference", 33 ed., Medical Economics Co., Oradell, N.J., U.S.A., 1979. For example, propranolol is administered daily to humans in a range of 80 to 640 mg, usually in the form of unit doses of 10, 20, 40 or 80 mg. When used in combination, the compound of formula I is administered as described previously.

The following reaction scheme illustrates a method for preparing the compounds of formula I.

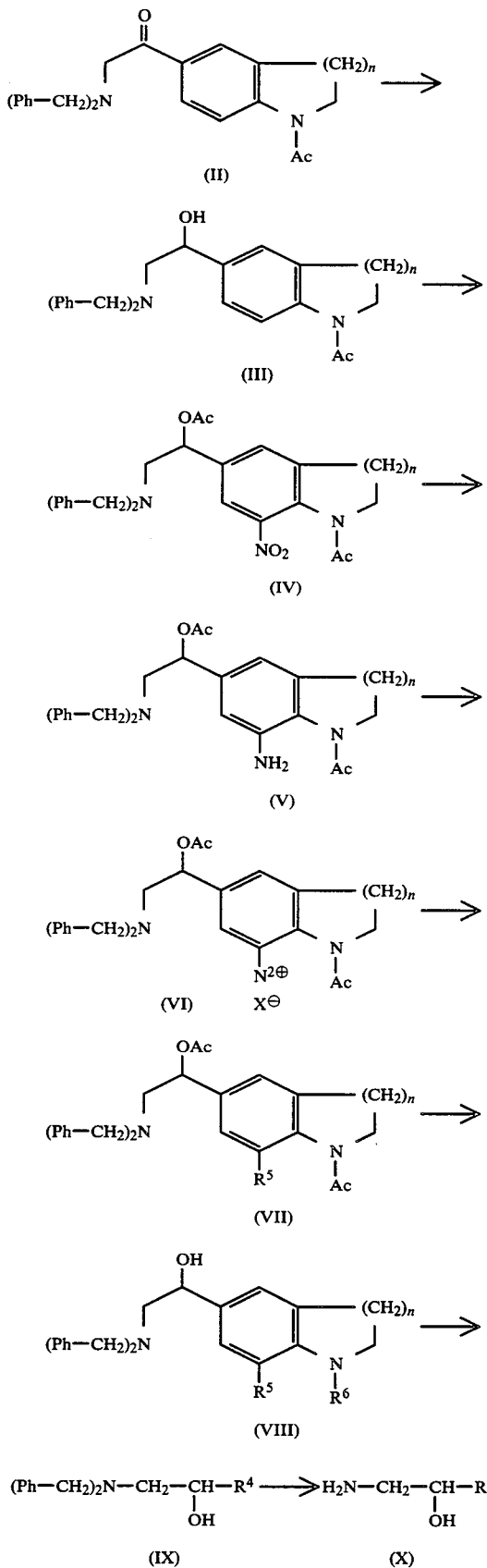

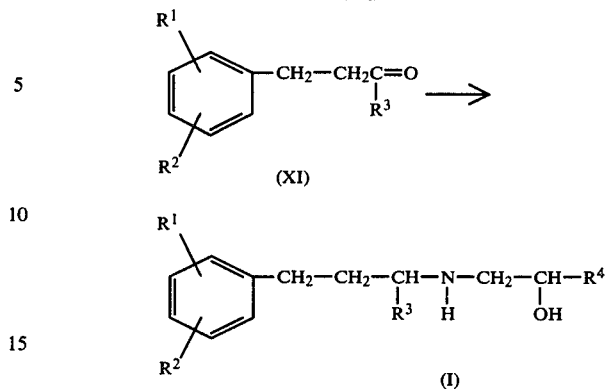

With reference to the above reaction scheme, the starting materials of formula II in which n is the integer 1 or 2 are readily prepared according to the method described by F. Troxler et al., Helv. Chim. Acta, 51, 1676 (1968). Reduction of the compound of formula II with a complex borohydride gives the corresponding compound of formula III in which n is as defined herein. The preferred method involves reducing the compound of formula II with about one to two molar equivalents of sodium borohydride in ethanol at about 0° to 50° C. for about one to five hours.

Acetylation, followed by nitration, of the compound of formula III affords the corresponding compound of formula IV in which n is as defined herein. The acetylation is achieved by reacting the compound of formula III with an excess of acetic anhydride and pyridine at about 20° to 30° C. for about two to ten hours. The resulting diacetyl compound is then nitrated with an excess of red fuming nitric acid in acetic acid at about 0° to 30° C. for two to five hours to obtain the corresponding compound of formula IV in which n is as defined herein.

Reduction of the compound of formula IV gives the corresponding amino compound of formula V in which n is as defined herein. One useful method of reduction involves reacting the compound of formula IV with about 1.5 molar equivalents of triirondodecacarbonyl in a solvent consisting of benzene and methanol at about 60° to 80° C. for about three to eight hours. In another method of reduction, the compound of formula IV is reduced with an excess of a mixture of calcium chloride, zinc dust and activated charcoal in aqueous ethanol at about 20° to 30° C. for about 30 minutes to two hours.

The amino compound of formula V is converted to the corresponding diazonium salt of formula VI in which n is as defined herein and $X^\ominus$ is $Cl^\ominus$ or $BF_4^\ominus$. For this conversion, a solution of the compound of formula V is treated with an excess of sodium nitrite in 15 to 20% hydrochloric acid at about $-10°$ to 0° C. to obtain the corresponding diazonium salt of formula VI in which X is $Cl^\ominus$. If an excess of fluoboric acid is added to the latter reaction mixture, the corresponding diazonium salt of formula VI in which X is $BF_4^\ominus$ readily precipitates from the reaction solution.

The diazonium salt of formula VI is useful for preparing a number of compounds of formula VII. If desired, the diazonium salt of formula VI in which $X^\ominus$ is $BF_4^\ominus$ can be reacted with an excess of a solution of potassium cyanide and copper (I) cyanide in dimethyl sulfoxide at about 10° to 25° C. for about one to five hours to obtain the corresponding compound of formula VII in which n is as defined herein and $R^5$ is cyano. In another conversion, the diazonium salt of formula VI in which $X^\ominus$ is $Cl^\ominus$ is reacted with an excess of sodium mercaptan and copper powder, according to the method of Von H. Zipp et al., Arzneim-Forsch/Drug Res., 31, 200 (1981), to obtain the corresponding compound of formula VII in which n is as defined herein and $R^5$ is methylthio. If desired, the diazonium salt of formula VI in which $X^\ominus$ is $Cl^\ominus$ can be reacted with sulfur dioxide to obtain an intermediate chlorosulfone and reaction of this chlorosulfone with ammonia gives the corresponding compound of formula VII in which n is as defined herein and $R^5$ is aminosulfonyl.

Alkaline hydrolysis of the compound of formula VII gives the corresponding compound of formula VIII in which n is as defined herein, $R^5$ is cyano, methylthio or aminosulfonyl and $R^6$ is hydrogen. For this hydrolysis, the compound of formula VII is reacted with a solution of about four to ten percent sodium or potassium hydroxide in aqueous ethanol at about 15° to 30° C. for about one to five hours.

If desired, the latter compound of formula VIII can be alkylated to obtain the corresponding compound of formula VIII in which n is as defined herein, $R^5$ is cyano, methylthio or aminosulfonyl and $R^6$ is lower alkyl. One useful method involves the reaction of the secondary amine of formula VIII with a lower alkyl bromide, chloride or iodide in the presence of sodium hydride in an inert organic solvent at 20° to 40° C.

In another conversion, the compound of formula VIII in which n and $R^6$ are as defined herein and $R^5$ is cyano is oxidized to obtain the corresponding compound of formula VIII in which n and $R^6$ are as defined herein and $R^5$ is aminocarbonyl. A useful method for conducting this oxidation involves treating the cyano compound of formula VIII with a solution containing powdered sodium hydroxide and 30 percent hydrogen peroxide in dimethyl sulfoxide at about 0° to 20° C. for about one half to one hour.

Aromatization of the compound of formula VIII in which n and $R^6$ are as defined herein and $R^5$ is cyano, aminocarbonyl, ethylthio or aminosulfonyl gives the corresponding compound of formula IX in which $R^4$ is heterocyclic selected from

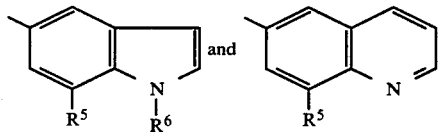

wherein $R^5$ is cyano, aminocarbonyl, methylthio or aminosulfonyl and $R^6$ is hydrogen or lower alkyl. A number of methods can be used to effect the aromatization. In one method, the compound of formula VIII is treated with a solution of chloranil in xylene at about 120° to 140° C. until the aromatization is complete. Similarly, in another method, the compound of formula VIII is aromatized with a mixture of five to ten percent palladium on charcoal in xylene at about 120° to 140° C. A particularly useful and preferred method of converting the compound of formula VIII in which n and $R^6$ are as defined herein and $R^5$ is cyano to the corresponding compound of formula IX in which $R^4$ is a heterocycle as defined immediately above wherein $R^5$ is aminocarbonyl and $R^6$ is hydrogen or lower alkyl involves treating the latter compound of formula VIII with a solution containing powdered sodium hydroxide in dimethyl sulfoxide at about 20° to 30° C. for about two to four hours and then adding a solution of about 25 to 30 percent hydrogen peroxide to the reaction mixture. The resulting reaction mixture is maintained at about 20° to 30° C. for about one to five hours and the compound of formula IX is recovered. In this manner, the cyano group is converted to the aminocarbonyl at the same time as the aromatization is achieved.

If desired, the compound of formula IX in which $R^4$ is a heterocycle as defined herein wherein $R^5$ is methylthio can be oxidized with hydrogen peroxide in acetic acid at about 10° C. to obtain the corresponding compound of formula IX wherein $R^5$ is methylsulfinyl. Further oxidation of the latter methylsulfinyl compound of formula IX with m-chlorobenzoic acid in acetone at about 20° to 30° C. affords the corresponding compound of formula IX in which $R^5$ is methylsulfonyl.

Removal of the benzyl protecting groups from the nitrogen in the compound of formula IX in which $R^4$ is a heterocycle as defined herein affords the corresponding compound of formula X in which $R^4$ is a heterocycle as defined herein. The benzyl protecting groups are readily removed by hydrogenating a mixture of the compound of formula IX and a hydrogenation catalyst, preferably ten percent palladium on carbon, in a lower alkanol, preferably methanol or ethanol, at about 20° to 30° C.

Condensation of the compound of formula X in which $R^4$ is as defined herein with the ketone of formula XI in which $R^1$, $R^2$ and $R^3$ are as defined herein gives the corresponding compound of formula I in which $R^1$, $R^2$, $R^3$ and $R^4$ are as defined herein. For this condensation, substantially equimolar amounts of the compounds of formulae X and XI are allowed to condense in an inert organic solvent, preferably methanol, at about 20° to 30° C. for about 10 to 40 minutes. The resulting enamine intermediate is then reduced to give the corresponding compound of formula I. One suitable reagent for this reduction is a complex borohydride, preferably about a molar equivalent of sodium cyanoborohydride at about 20° to 30° C. for about 15 to 30 hours. This reduction can also be achieved by hydrogenation in the presence of a hydrogenation catalyst, preferably ten percent palladium on charcoal or platinum oxide, or mixtures thereof. In the latter condensation and reductions, the presence of an acid, for example, hydrogen chloride, hydrogen bromide, or acetic acid, will result in increased yields and shorter reaction times.

In a preferred method of preparing the compound of formula I, the benzyl groups are removed from the compound of formula IX and the compounds of formulae X and XI are condensed simultaneously in the same reaction mixture. This method involves hydrogenating a mixture of about equimolar amounts of the compound of formula IX and an acid, preferably acetic acid, with an excess of the compound of formula XI in the presence of a hydrogenation catalyst, preferably a mixture of ten percent palladium on charcoal and ten percent platinum oxide, in an inert organic solvent, preferably methanol or ethanol, at about 20° to 30° C. for about 10 to 30 hours. From this reaction mixture, the compound of formula I is isolated.

The following example illustrates further this invention.

EXAMPLE

Preparation of 5-[1-hydroxy-2-[(1-methyl-3-phenylpropyl)amino]ethyl]-1H-indole-7-carboxamide (I: $R^1$ and $R^2$=H, $R^3$=Me and $R^4$=7-aminocarbonyl-1H-indol-5-yl)

1-Acetylindoline (A16.1 g, 0.1 mol) and chloroacetylchloride (14.0 g, 9.6 mL, 0.12 mol) were added to carbon disulfide (200 mL) and heated to 40° C. Aluminium trichloride (42 g, 0.315 mol) was added portionwise to the mechanically stirred solution. After the addition was complete, the mixture was refluxed for 2 hours. The carbon disulfide was decanted and the remaining traces of carbon disulfide were evaporated using a stream of nitrogen while stirring the mixture (1 hour). Ice was added (exothermic!) to the dark green slurry with stirring under nitrogen. The ice mixture was stirred until a white homogenous mixture was obtained. The solid (32 g) was collected, washed with water, dried in air and reacted as such with dibenzylamine (60 g, 0.31 mol) at reflux temperature in dry acetonitrile (650 mL) overnight. The resulting mixture was cooled (10° C.) and dichloromethane (650 mL) was added. The precipitate was filtered, and the filtrate was concentrated to dryness. The residue was triturated with diethyl ether to afford a yellow solid (34.24 g) of 1-(1-acetyl-2,3-dihydro-1H-indol-5-yl)-2-[bis(phenylmethyl)amino]-ethanone: mp 130° C. (crystallized from ethyl acetate) and NMR (CDCl$_3$)δ 2.2 (s, 3H), 3.1 (t, 2H), 3.7 (s, 6H), 4.05 (t, 2H), 7.4 (m, 13H).

To a solution of the latter compound (35.00 g, 70 mmol), in absolute ethanol (700 mL) at 0° C., sodium borohydride (3.53 g, 93 mmol) was added. The reaction mixture was stirred at 0° C. for 1 hour, at room temperature for 15 hr and at 50° C. for 1 hour. Buffer (pH=4.0) was added until pH=7.5 was obtained and the solution was stirred for an additional 0.5 hour. The product was extracted with diethyl ether (3×100 mL), and the extract was washed with water (3×100 mL), dried (MgSO$_4$) and concentrated to afford the product as a white solid. Recrystallization from diethyl ether gave 1-acetyl-5-[2-(dibenzylamino)-1-hydroxyethyl]indoline (30.04 g): mp 116° C.; Anal. Calcd for C$_{26}$H$_{28}$N$_2$O$_2$: C, 77.97% H, 7.05% N, 7.00% and Found: C, 77.38% H, 6.98% N, 6.89%.

A solution of the latter compound (10.0 g, 25 mmol) in acetic anhydride (50 mL) and pyridine (10 mL) was stirred at room temperature for 4 hours. The solvents were evaporated under vacuum. The residue was dissolved in dichloromethane, and the solution was washed with a sodium bicarbonate solution, water, dried (MgSO$_4$) and evaporated to give an oil (11.68 g). A sample (18.85 g) was crystallized out of diethyl ether to give an off-white solid (7.0 g) of 1-acetyl-5-[2-(dibenzylamino)-1-acetyloxyethyl]-indoline: mp 91°–92° C. and NMR (CDCl$_3$)δ 2.01 (s, 3H), 2.18 (s, 3H), 2.77 (m, 2H), 3.60 (t, 2H), 3.59 (s, 4H), 4.00 (t, 2H), 5.85 (t, 1H), 6.85–7.3 (m, 12H), 8.05 (d, 1H).

A solution of the latter compound (4.42 g, 10 mmol) in glacial acetic acid (20.6 mL) was treated dropwise with red fuming nitric acid (2.95 mL) at 5° C., and the reaction mixture was then stirred at room temperature for 2.5 hours. After completion of the reaction, water (150 mL) was added and the product was extracted with dichloromethane. The combined organic phase was basified with a sodium carbonate solution, washed with water, dried over magnesium sulfate and evaporated to give a yellow foam (5.04 g) which was crystallized from an ethanol-diethyl ether mixture to give 1-acetyl-5-[2-(dibenzylamino)-acetyloxyethyl]-7-nitroindoline: mp 109°–111° C. and NMR (CDCl$_3$)δ 2.00 (s, 3H), 2.22 (s, 3H), 2.76 (m, 2H), 3.06 (t, 2H), 3.59 (s, 4H), 4.17 (t, 2H), 5.76 (t, 2H), 7.2 (M, 12H).

The latter compound (10.21 g, 20.9 mmol) was refluxed for 4 hours under a nitrogen atmosphere in dry benzene (167 mL) containing triirondodecacarbonyl (13.70 g, 27 mmol) and methanol (4.6 mL). The solution was cooled to room temperature, filtered, washed with water, dried and evaporated to afford an oil (9.24 g). Purification through a column of silica gel using petroleum ether-ethyl acetate (35-65) as the eluant afforded 1-acetyl-5-[2-(dibenzylamino)-acetyloxyethyl]indolin-7-amine (7.81 g): NMR (CDCl$_3$)δ 2.01 (s, 3H), 2.25 (s, 3H), 2.75 (m, 2H), 2.93 (t, 2H), 3.61 (s, 4H), 3.99 (t, 2H), 4.72 (br s, 2H), 5.81 (m, 1H), 6.30 (d, 1H), 6.38 (d, 1H), 7.22 (s, 10H).

To a solution of the latter compound (4.57 g, 0.01 mol), concentrated hydrochloric acid (18 mL) and water (18 mL) at 5° C., was added dropwise a solution of sodium nitrite (2.58 g) in water (6 mL) over a 10 min period. The mixture was then treated dropwise with 24% fluoboric acid (36 mL), and a precipitate formed after stirring at −5° C. The yellow diazonium salt (8.77 g) was collected by filtration, washed with cold HBF$_4$ (20 mL), methanol (40 mL) and diethyl ether (20 mL), and used immediately for the next step. A sample crystallized from boiling methanol upon cooling to give 1-acetyl-5-[2-(dibenzylamino)-1-acetyloxyethyl]-indoline-7-diazonium fluoborate: mp 145°–153° C. and NMR (DMSO-d$_6$)δ 2.05 (s, 3H), 2.35 (s, 3H), 3.25 (m, 4H), 4.35 (m, 4H), 5.1 (br, 2H), 5.8 (t, 1H), 7.4 (br, 10H), 7.75 (s, 2H), 8.0 (s).

A solution of the latter compound (8.77 g, prepared from 0.01 mol of amine) in dimethyl sulfoxide (66 mL) was added dropwise over a 45 min period at 14° C. to a previously prepared viscous solution of potassium cyanide (18 g) and copper (I) cyanide (21.5 g) in dimethyl sulfoxide (130 mL). The ice bath was replaced by a water bath at 22° C., and the mixture was stirred for an additional 45 min. Cold water (1000 mL) was added to the red solution and the product was extracted with dichloromethane. The combined organic phase was washed with water, dried over MgSO$_4$ and evaporated to give a crude product (4.32 g). Purification through a column of silica gel using petroleum ether:ethyl acetate (50:50) as the eluant afforded the pure product (3.26 g). A sample was crystallized from ethanol-petroleum ether to give 1-acetyl-5-[2-(dibenzylamino)-1-acetyloxyethyl]-7-cyanoindoline: mp 108°–109° C. and NMR (CDCl$_3$)δ 2.02 (s, 3H), 2.29 (s, 3H), 2.76 (m, 2H), 3.01 (t, 2H), 3.61 (s, 4H), 4.1 (t, 2H), 5.73 (t, 1H), 7.2 (m, 12H).

A solution of the latter compound (1.69 g, 3.6 mmol) in ethyl alcohol (100 mL) was treated with 5N aqueous sodium hydroxide (6.73 mL) at room temperature for 2 hours. Brine (200 mL) was added and the product was extracted with diethyl ether (3×150 mL). The combined organic phase was washed with water, dried over magnesium sulfate and concentrated. Purification through a column of silica gel using ethyl acetate-petroleum ether (25-75) as the eluant afforded the pure product as an oil (1.18 g). A sample was crystallized from ethyl acetate and petroleum ether to give 5-[1-hydroxy-2-(dibenzylamino)ethyl]-7-cyanoindoline; mp 139°–140° C. and NMR (CDCl$_3$)δ 2.55 (d, 2H), 3.00 (t, 2H), 3.30–3.95 (m, 6H), 4.5 (m, 2H).

A solution of the latter compound (1.29 g, 3.4 mmol), powdered sodium hydroxide (4.9 g) and dry dimethyl sulfoxide (85 mL) was stirred at room temperature for 3 hours. The reaction mixture was cooled to 0° C. and treated dropwise with 30% hydrogen peroxide (15 mL). After stirring for 1.5 hour at room temperature, water (800 mL) was added and the product was extracted with ethyl acetate (3x). The combined ethyl acetate fractions were washed with water, dried ($MgSO_4$) and concentrated to afford an oil. Purification through a column of silica gel using petroleum ether-ethyl acetate (45:55)+4% $NH_4OH$ as the eluant afforded a solid (0.920 g). A sample was crystallized out of ethyl acetate and diethyl ether to give 5-[2-(dibenzylamino)-1-hydroxyethyl]-indole-7-carboxamide: mp 116°–118° C. and NMR ($CDCl_3$)δ 2.68 (d, 2H), 3.05 (br, 1H), 3.4 and 3.9 (doublets, 4H), 4.80 (t, 1H), 5.90 (br, 2H), 6.45 (m, 1H), 7.1–7.4 (m, 12H), 7.6 (s, 1H).

A solution of the latter compound (2.60 g, 6.5 mmol), benzylacetone (1.58 g, 10 mmol) and acetic acid (0.2 mL) in methanol (244 mL) was hydrogenated in the presence of 10% Pd/C (0.500 g) and 10% $PtO_2$ (0.500 g) catalysts. After 6 hour and 14 hours, more benzylacetone (1.5 g and 1.0 g) was added. Reaction was followed by tlc, and catalysts and solvents were removed after completion. Purification through a column of silica gel using methanol-chloroform (85:15)+0.5% $NH_3$ as the eluant afforded the title compound as a white solid (1.49 g) mp 94°–100° C; IR (mineral oil) 3420, 3180 and 1650 $cm^{-1}$; UV max (methanol) 312 nm (ε 7,090) and 231 (22,960); NMR ($CDCl_3$)δ 1.07 (d, 3H), 1.65 (m, 2H), 2.65 (m, 5H), 4.72 (two d, 1H), 6.23 (2H), 6.46 (t, 1H), 7.25 (m, 6H), 7.48 (s, 1H), 7.67 (s, 1H) and 10.20 (s, 1H); and Anal. Calcd for $C_{21}H_{25}N_3O_2 \cdot H_2O$: C, 68.27% H, 7.37% N, 11.37% and Found: C, 68.41% H, 7.40% N, 11.66%.

The title compound was also obtained by the following method.

A solution of 5-[2-(dibenzylamino)-1-hydroxyethyl]-indole-7-carboxamide (119.7 mg, 0.3 mmol, described above) was hydrogenated for 28 hours at atmospheric pressure and room temperature in dry methanol (12.0 mL) containing 10% palladium on carbon. The mixture was filtered and the filtrate was evaporated. Crystallization from an ethyl acetate-diethyl ether mixture gave 5-(2-amino-1-hydroxyethyl)indole-7-carboxamide: mp 88°–90° C.; and NMR ($DMSO-d_6$)δ 2.70 (d, 2H), 2.80–3.60 (br s, 5H), 4.50 (t, 1H), 6.40 (m, 1H), 7.00–7.70 (m, 3H) and 10.75 (br s, 1H).

To a solution of the latter amine (0.12 g, 0.54 mmol) in dry methanol (3 mL) was added 5N methanolic hydrogen chloride (0.12 mL, 0.59 mmol) under stirring, followed by benzylacetone (0.080 g, 0.81 mL, 0.54 mmole) at room temperature. After 15 min, sodium cyanoborohydride (0.034 g, 0.54 mmol) was added and the solution was stirred at room temperature for 24 hours, neutralized with aqueous sodium bicarbonate to pH 7, saturated with salt and extracted with diethyl ether (3×40 mL). The combined extracts were dried ($MgSO_4$) and concentrated. The residue was purified by column chromatography through silica gel using the following mixture as eluant: benzene (50)-ethyl acetate(40)-methanol(5)-triethylamine(5). Trituration of the residue with dichloromethane-petroleum ether gave the title compound as a solid (0.067 g).

We claim:

1. A compound of the formula

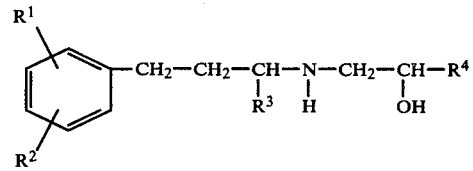

in which $R^1$ and $R^2$ each is hydrogen, halogen or lower alkoxy, or adjacent $R^1$ and $R^2$ are joined together to form a methylenedioxy chain; $R^3$ is lower alkyl containing one to three carbon atoms; and $R^4$ is a heterocycle selected from the group consisting of

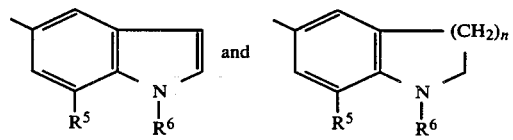

wherein n is the integer 1; $R^5$ is carboxamide and $R^6$ is hydrogen or lower alkyl; or a therapeutically acceptable acid addition salt thereof.

2. A compound of claim 1 wherein $R^1$ and $R^2$ each is hydrogen or lower alkoxy, or adjacent $R^1$ and $R^2$ are joined together to form a methylenedioxy chain; $R^3$ is methyl; and $R^4$ is the heterocycle

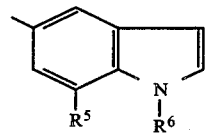

wherein $R^5$ is carboxamide and $R^6$ is hydrogen or lower alkyl.

3. 5-[1-Hydroxy-2-[(1-methyl-3-phenylpropyl)amino]ethyl]-1H-indole-7-carboxamide, a compound of claim 1.

4. 5-[1-Hydroxy-2-[(1-methyl-3-phenylpropyl)amino]ethyl]-1H-2,3-dihydroindole-7-carboxamide, a compound of claim 1.

5. A method of treating hypertension in a hypertensive mammal, which comprises administering to said mammal an effective antihypertensive amount of a compound of claim 1.

6. A pharmaceutical composition, useful for the treatment of hypertension, which comprises a compound of claim 1, and a pharmaceutically acceptable carrier therefor.

* * * * *